United States Patent
Li et al.

(10) Patent No.: US 10,665,221 B2
(45) Date of Patent: May 26, 2020

(54) VIRTUAL REALITY GUIDE HYPNOSIS SPEECH PROCESSING METHOD AND APPARATUS

(71) Applicant: SHENZHEN INSTITUTES OF ADVANCED TECHNOLOGY CHINESE ACADEMY OF SCIENCES, Shenzhen, Guangdong (CN)

(72) Inventors: Rongmao Li, Guangdong (CN); Shanshan Zang, Guangdong (CN); Yanjun Liu, Guangdong (CN); Yili Chen, Guangdong (CN); Yanchun Zhu, Guangdong (CN); Mingmin Chen, Guangdong (CN); Yaoqin Xie, Guangdong (CN)

(73) Assignee: SHENZHEN INSTITUTES OF ADVANCED TECHNOLOGY CHINESE ACADEMY OF SCIENCES, Shenzhen (CN)

(*) Notice: Subject to any disclaimer, the term of this patent is extended or adjusted under 35 U.S.C. 154(b) by 315 days.

(21) Appl. No.: 15/856,349

(22) Filed: Dec. 28, 2017

(65) Prior Publication Data

US 2018/0122362 A1 May 3, 2018

Related U.S. Application Data

(63) Continuation of application No. PCT/CN2016/100780, filed on Sep. 29, 2016.

(51) Int. Cl.
G10L 13/04 (2013.01)
G10L 13/047 (2013.01)
(Continued)

(52) U.S. Cl.
CPC .......... *G10L 13/043* (2013.01); *A61M 21/02* (2013.01); *G06F 40/253* (2020.01); *G06F 40/30* (2020.01);
(Continued)

(58) Field of Classification Search
CPC .......... A61M 21/02; A61M 2021/0027; G10L 13/047; G10L 13/043; G10L 13/10; G09B 9/00; G06F 17/2785; G06F 17/274
See application file for complete search history.

(56) References Cited

U.S. PATENT DOCUMENTS

2001/0005770 A1* 6/2001 Blumenthal .......... A61M 21/00
    600/27
2009/0319301 A1* 12/2009 Hyde .................. G06F 19/3456
    705/3

FOREIGN PATENT DOCUMENTS

| CN | 201286926 | 8/2009 |
| CN | 102430182 | 5/2012 |
| CN | 105536119 | 5/2016 |

* cited by examiner

*Primary Examiner* — Christine H Matthews
*Assistant Examiner* — Joshua Daryl D Lannu
(74) *Attorney, Agent, or Firm* — Bayramoglu Law Offices LLC

(57) ABSTRACT

A virtual reality guide hypnosis speech processing method and apparatus, wherein the method comprises: performing a text analysis for a hypnosis guide language, so as to obtain text hierarchical information of the hypnosis guide language; performing a speech analysis for the hypnosis guide language, so as to obtain speech rhythm information of the hypnosis guide language; searching a hypnosis speech library for corresponding speech units, according to the text hierarchical information and the speech rhythm information of the hypnosis guide language, the hypnosis speech library storing speech units generated according to corpus data (Continued)

recorded by a user's susceptible person; synthesizing found speech units into hypnosis speech data; and synthesizing the hypnosis speech data with a virtual reality hypnosis scene, and outputting a virtual reality guide hypnosis speech. The present disclosure can improve the user's hypnosis susceptibility and optimize the hypnosis effect.

12 Claims, 3 Drawing Sheets

(51) Int. Cl.
　　*G06F 17/27*　　(2006.01)
　　*A61M 21/02*　　(2006.01)
　　*G09B 9/00*　　(2006.01)
　　*G06F 40/30*　　(2020.01)
　　*G06F 40/253*　　(2020.01)
　　*G10L 13/10*　　(2013.01)
　　*A61M 21/00*　　(2006.01)

(52) U.S. Cl.
　　CPC ................ G09B 9/00 (2013.01); G10L 13/10 (2013.01); *A61M 2021/0027* (2013.01); *G10L 13/047* (2013.01)

VIRTUAL REALITY GUIDE HYPNOSIS SPEECH PROCESSING METHOD AND APPARATUS

This application is a continuation of International Application No. PCT/CN2016/100780, filed on Sep. 29, 2016, which is hereby incorporated by reference in its entirety.

TECHNICAL FIELD

The present disclosure relates to the technical field of virtual reality guide hypnosis, and particularly, to a virtual reality guide hypnosis speech processing method and apparatus.

BACKGROUND

The existed virtual reality guide hypnosis technologies generally synthesize a fixed standardized hypnosis speech (recorded by a professional announcer) with a virtual reality hypnosis scene, so as to guide a user to enter a hypnosis state. Although the tone, the timbre, etc. are more relevant to the speech requirement of the hypnosis process when the user is guided into hypnosis with the fixed standardized hypnosis speech, the user's requirement of faster and better hypnosis cannot be satisfied, and the hypnosis effect is not good.

SUMMARY OF THE DISCLOSURE

The embodiments of the present disclosure provide a virtual reality guide hypnosis speech processing method, for improving the user's hypnosis susceptibility and optimizing the hypnosis effect, comprising:

performing a text analysis for a hypnosis guide language, so as to obtain text hierarchical information of the hypnosis guide language;

performing a speech analysis for the hypnosis guide language, so as to obtain speech rhythm information of the hypnosis guide language;

searching a hypnosis speech library for corresponding speech units, according to the text hierarchical information and the speech rhythm information of the hypnosis guide language, the hypnosis speech library storing speech units generated according to corpus data recorded by a user's susceptible person;

synthesizing found speech units into hypnosis speech data;

synthesizing the hypnosis speech data with a virtual reality hypnosis scene, and outputting a virtual reality guide hypnosis speech.

The embodiments of the present disclosure further provide a virtual reality guide hypnosis speech processing apparatus, for improving the user's hypnosis susceptibility and optimizing the hypnosis effect, comprising: a memory, a processor and a computer program stored in the memory and executable in the processor, wherein the processor performs the following operations when executing the computer program:

performing a text analysis for a hypnosis guide language, so as to obtain text hierarchical information of the hypnosis guide language;

performing a speech analysis for the hypnosis guide language, so as to obtain speech rhythm information of the hypnosis guide language;

searching a hypnosis speech library for corresponding speech units, according to the text hierarchical information and the speech rhythm information of the hypnosis guide language, the hypnosis speech library storing speech units generated according to corpus data recorded by a user's susceptible person;

synthesizing found speech units into hypnosis speech data;

synthesizing the hypnosis speech data with a virtual reality hypnosis scene, and outputting a virtual reality guide hypnosis speech.

The embodiments of the present disclosure further provide a computer readable storage medium, improving the user's hypnosis susceptibility and optimizing the hypnosis effect, wherein the computer readable storage medium stores a computer program which causes the processor to perform the following operations when being executed:

performing a text analysis for a hypnosis guide language, so as to obtain text hierarchical information of the hypnosis guide language;

performing a speech analysis for the hypnosis guide language, so as to obtain speech rhythm information of the hypnosis guide language;

searching a hypnosis speech library for corresponding speech units, according to the text hierarchical information and the speech rhythm information of the hypnosis guide language, the hypnosis speech library storing speech units generated according to corpus data recorded by a user's susceptible person;

synthesizing found speech units into hypnosis speech data;

synthesizing the hypnosis speech data with a virtual reality hypnosis scene, and outputting a virtual reality guide hypnosis speech.

The embodiments of the present disclosure take into account the matching between the hypnosis process speech and the user's hypnosis susceptibility, employ the speech synthesis technology to change the original standardized hypnosis speech and synthesize the speech of the user's susceptible person, while combining the hypnosis guide characteristics, and finally output the hypnosis speech susceptible to the user, thereby improving the user's hypnosis susceptibility, and optimizing the hypnosis effect. Meanwhile, the embodiments of the present disclosure provide a solution of automatic speech synthesis, which avoids the tedious live manual recording, meets the user requirement, helps the crowds having no hypnosis knowledge background to automatically output the hypnosis speech to finish the hypnosis process, and helps the user to better enter the hypnosis state.

BRIEF DESCRIPTION OF THE DRAWINGS

In order to more clearly describe the technical solutions in the embodiments of the present disclosure, the drawings to be used in the descriptions of the embodiments will be briefly introduced as follows. Obviously, the drawings in the following descriptions just illustrate some embodiments of the present disclosure, and a person skilled in the art can obtain other drawings from them without paying any creative effort. In which.

DETAILED DESCRIPTION OF THE EMBODIMENTS

In order that the objectives, technical solutions and advantages of the embodiments of the present disclosure are clearer, the embodiments of the present disclosure will be further described in details as follows with reference to the drawings. Here the exemplary embodiments of the present disclosure and descriptions thereof are just used to explain, rather than limiting, the present disclosure.

The inventor considers that the existed virtual reality guide hypnosis technologies use the fixed standardized hypnosis speech, which cannot satisfy the user's requirement and the hypnosis effect is influenced, while if the matching between the speech of the hypnosis process and the user's hypnosis susceptibility is taken into account, the expected effect can be achieved faster and better. On the other hand, the user's hypnosis susceptible sound object usually has no professional hypnotic technical background and cannot provide the user with a professional and effective hypnosis guide process. In view of this, the embodiments of the present disclosure provide a virtual reality guide hypnosis speech processing method, which optimizes the hypnosis effect by improving the user's hypnosis susceptibility.

Figure 1:
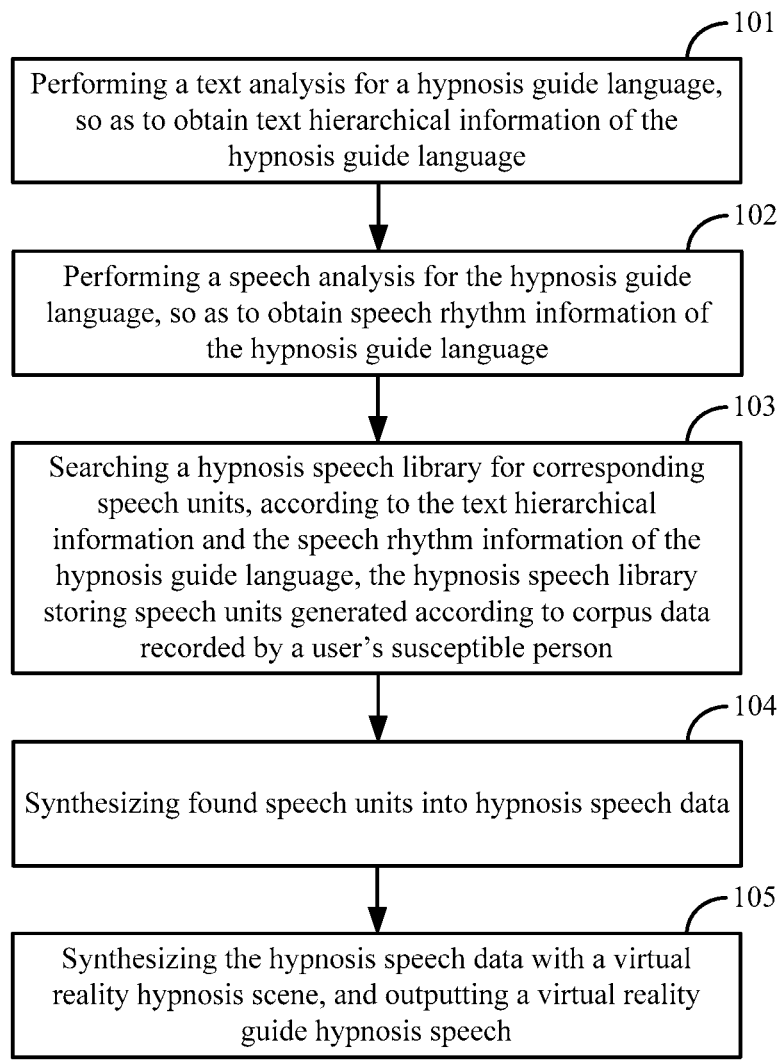
FIG. 1 is a schematic diagram of a virtual reality guide hypnosis speech processing method in an embodiment of the present disclosure.

FIG. 1 is a schematic diagram of a virtual reality guide hypnosis speech processing method in an embodiment of the present disclosure. As shown in FIG. 1, the method comprises:

step 101: performing a text analysis for a hypnosis guide language, so as to obtain text hierarchical information of the hypnosis guide language;

step 102: performing a speech analysis for the hypnosis guide language, so as to obtain speech rhythm information of the hypnosis guide language;

step 103: searching a hypnosis speech library for corresponding speech units, according to the text hierarchical information and the speech rhythm information of the hypnosis guide language, the hypnosis speech library storing speech units generated according to corpus data recorded by a user's susceptible person;

step 104: synthesizing found speech units into hypnosis speech data;

step 105: synthesizing the hypnosis speech data with a virtual reality hypnosis scene, and outputting a virtual reality guide hypnosis speech.

As can be seen from the procedure of FIG. 1, the embodiment of the present disclosure sufficiently considers that different hypnosis sound characteristics employed for the user in the guide hypnosis process will have different influences on the user's hypnosis effect, wherein the user can easily enter a particular hypnosis state when the speech of the user's susceptible person is used, so as to achieve a better hypnosis effect. Meanwhile, the embodiments of the present disclosure provide a solution of automatic speech synthesis, which avoids the tedious live manual recording, achieves a phased objective that the hypnosis is completely produced by machines, and can output the hypnosis speech having the speech characteristics of the user's susceptible person, thereby meeting the user requirement. On the other hand, by virtue of the speech synthesis technology, the embodiments of the present disclosure can help the crowds having no hypnosis knowledge background to automatically output a hypnosis speech to finish the hypnosis process, and help the user to better enter a hypnosis state.

In this embodiment, the corpus data of the user's susceptible person can be collected at the earlier stage, so as to establish a hypnosis speech library that stores speech units generated according to the corpus data recorded by the user's susceptible person. In this embodiment, the corpus data may be designed according to the hypnosis speech feature to be output. Next, the user's susceptible person records the corpus data under a particular requirement, and then the recorded corpus data is analyzed and set to establish the required hypnosis speech library. In this embodiment, the corpus data may be recorded by the user's susceptible person according to the hypnosis speech feature. The user's susceptible person records the corpus data according to the hypnosis speech feature under a particular requirement. For example, when the corpus data is to be recorded, the recording person is required to have uniform volume, gentle speed, clear pronunciation and mild emotion. The corpus data may also be recorded by the user's susceptible person at specified sampling rate and speech resolution. For example, the recording person is required to record a high signal-to-noise ratio speech at particular sampling rate and speech resolution, so that the corpus data is more standard.

Moreover, in consideration that the embodiment of the present disclosure intends to solve, by virtue of the speech synthesis technology, the problem that hypnosis effect will be affected when the user is unfamiliar and insensitive to the hypnotist's speech in the virtual reality guide hypnosis process, and automatically output user's hypnosis susceptible sounds in the virtual reality guide hypnosis process using the speech synthesis technology, so as to establish an emotional connection with the user in the aspect of language characteristics and optimize the hypnosis effect; the user's dialect or the sound of a trusted person enables the user to enter a particular hypnosis state more easily, so as to achieve a better hypnosis effect. Thus the corpus data may be recorded by the user's susceptible person with a dialect and/or a personalized language. In this way, the user's requirement is satisfied by outputting a personalized hypnosis speech having local features. As the key of the introduction of the speech synthesis technology in the embodiment of the present disclosure is to output a speech of the user's hypnosis susceptible person, it is suggested to select the recording person of the earlier corpus data particularly.

After the user's susceptible person records the corpus data, a hypnosis speech library is established and updated in real time according to the corpus data recorded by the user's susceptible person. In the process of establishing and updating the hypnosis speech library, the Hidden Markov Model may be used to divide the corpus data in the hypnosis speech library, so as to construct the speech units.

When the virtual reality guide hypnosis speech is to be output, firstly it needs to perform a text analysis for a hypnosis guide language, so as to obtain text hierarchical information of the hypnosis guide language; and then perform a speech analysis for the hypnosis guide language, so as to obtain speech rhythm information of the hypnosis guide language, wherein performing a text analysis for a hypnosis guide language, so as to obtain text hierarchical information of the hypnosis guide language for example may comprise: performing a text language analysis, a grammatical analysis and a semantic analysis of the hypnosis guide language, so as to obtain information of words, word groups and sentences in the hypnosis guide language and information of relations between the words, the word groups and the sentences in the hypnosis guide language.

In the specific embodiment, when a text analysis and a phonetic level rhythm analysis are to be performed for the hypnosis guide language, firstly, a text analysis may be performed for the text version of the hypnosis guide language, in the aspects of language level, grammatical level, semantic level, etc., respectively, so as to obtain hierarchical information of the hypnosis guide language, i.e., hierarchical relations between word groups, phrases, sentences, etc.; for example, in conjunction with the characteristics of virtual reality hypnosis, a hypnosis guide language completed through a negotiation with the professional hypnotist mainly includes a progressive relaxation guide, a hypnosis scene guide, etc., and word groups, phrases, sentences and the like in the hypnosis guide language are obtained through the grammatical and semantic analyses of the text information. Next, a rhythm analysis is performed based on the phonetic level of the hypnosis guide language, e.g., information such as the timbre, intonation, loudness, etc. of the sounds corresponding to the hypnosis guide language are analyzed to obtain rhythm information in the phonetic level.

After the text hierarchical information and the speech rhythm information of the hypnosis guide language is obtained, the hypnosis speech library is searched for corresponding speech units according to the text hierarchical information and the speech rhythm information of the hypnosis guide language, and the found speech units are synthesized into hypnosis speech data. In this embodiment, the found speech units may be selected, spliced and synthesized using a Hidden Markov Model. Corresponding synthetic processing is performed on the speech units extracted from the hypnosis speech library to obtain the required speech data, i.e., the hypnosis speech data susceptible to the user. In a specific example, the hypnosis guide language is output in a mild and sentient way, thus the speech synthesis process requires a speed control and an emotion attachment to the hypnosis speech.

Finally, the hypnosis speech data is synthesized with the virtual reality hypnosis scene to output a virtual reality guide hypnosis speech. For example, under a guidance of the professional hypnotist, the synthesized hypnosis speech data may be adjusted, optimized and finalized, and then guided into the virtual reality hypnosis scene, so as to output the virtual reality guide hypnosis speech.

Figure 2:
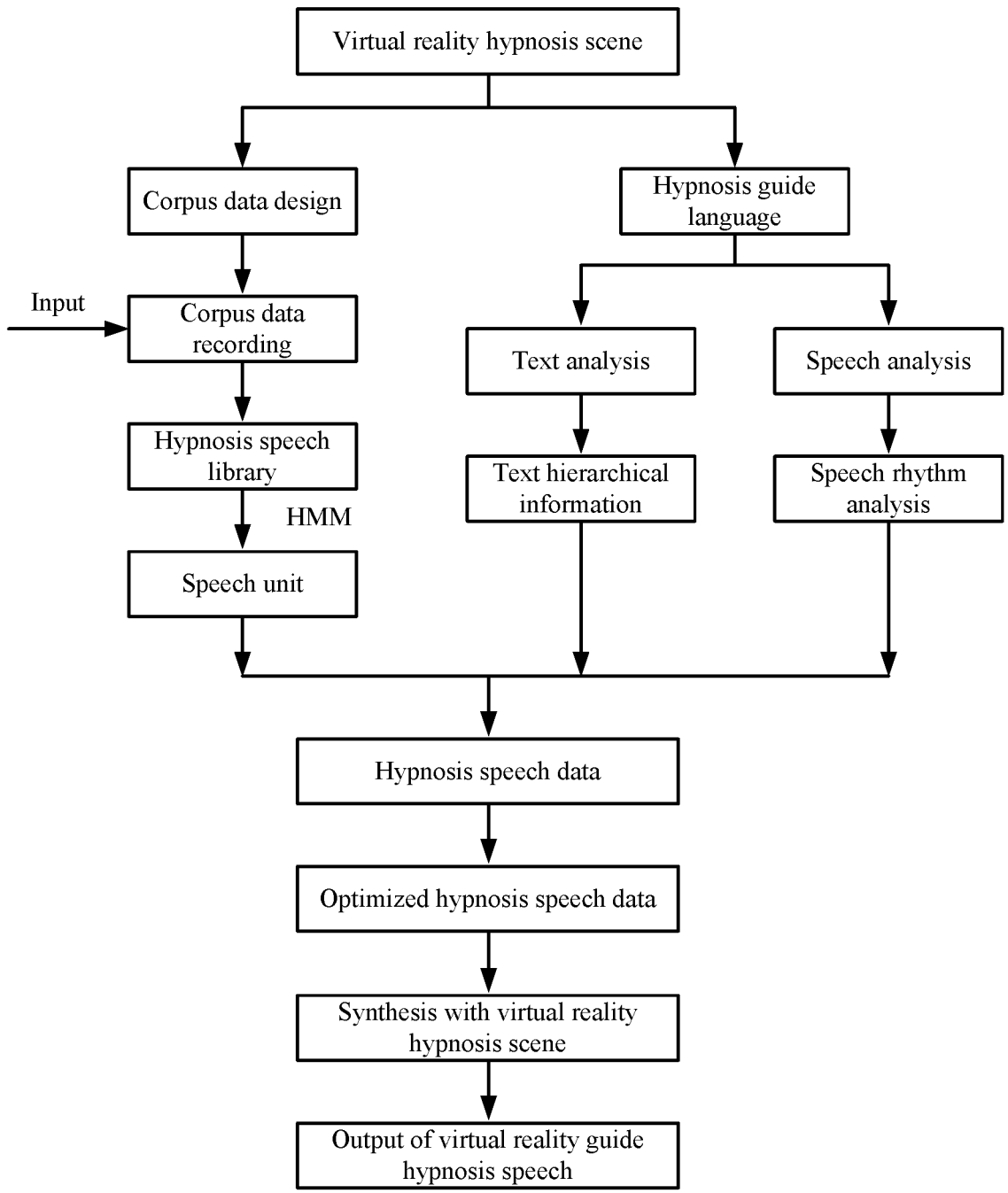
FIG. 2 is a schematic diagram of a specific example of a virtual reality guide hypnosis speech processing method in an embodiment of the present disclosure.

FIG. 2 is a schematic diagram of a specific example of a virtual reality guide hypnosis speech processing method in an embodiment of the present disclosure. As shown in FIG. 2, in this example, firstly corpus data is designed for a virtual reality hypnosis scene, and recorded corpus data is input by a user's susceptible person to establish a hypnosis speech library, while speech units are constructed using a Hidden Markov Model and stored in the hypnosis speech library; after a hypnosis guide language is determined, a text analysis is performed for the hypnosis guide language to obtain text hierarchical information thereof, and a speech analysis is performed for the hypnosis guide language to obtain speech rhythm information thereof; next, the hypnosis speech library is searched for corresponding speech units according to the text hierarchical information and the speech rhythm information of the hypnosis guide language, and found speech units are synthesized into hypnosis speech data; the hypnosis speech data is optimized and synthesized with the virtual reality hypnosis scene to finally output a virtual reality guide hypnosis speech.

As can be seen from the above embodiment, the embodiment of the present disclosure employs a voice synthesis technology, and collects the corpus data of the user's susceptible person at the earlier stage to obtain particular sentences of the user's hypnosis susceptible sounds, thereby establishing the hypnosis speech library; next, only text information shall be provided for the speech analysis, the speech unit extraction and synthesis, etc.; and finally a hypnosis speech of a person more susceptible to the user is output to improve the hypnosis effect. The hypnosis process adds an emotional dimension based on the original hypnosis effect to enhance the user's emotion cognition, thereby improving the hypnosis effect.

On the basis of the same invention concept, the embodiments of the present disclosure further provide a virtual reality guide hypnosis speech processing apparatus, as described in the following embodiment. Since the principle of the apparatus to solve the problem is similar to that of the virtual reality guide hypnosis speech processing method, please see the implementation of the virtual reality guide hypnosis speech processing method for the implementation of the apparatus, and the repeated content is omitted herein.

Figure 3:
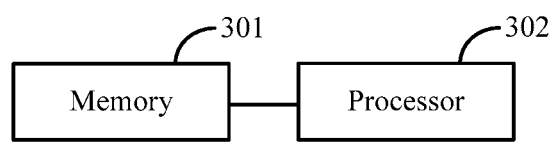
FIG. 3 is a schematic diagram of a virtual reality guide hypnosis speech processing apparatus in an embodiment of the present disclosure.

FIG. 3 is a schematic diagram of a virtual reality guide hypnosis speech processing apparatus in an embodiment of the present disclosure. As shown in FIG. 3, the apparatus may comprise a memory 301, a processor 302 and a computer program stored in the memory 301 and executable in the processor 302, wherein the processor 302 performs the following operations when executing the computer program:

performing a text analysis for a hypnosis guide language, so as to obtain text hierarchical information of the hypnosis guide language;

performing a speech analysis for the hypnosis guide language, so as to obtain speech rhythm information of the hypnosis guide language;

searching a hypnosis speech library for corresponding speech units, according to the text hierarchical information and the speech rhythm information of the hypnosis guide language, the hypnosis speech library storing speech units generated according to corpus data recorded by a user's susceptible person;

synthesizing found speech units into hypnosis speech data;

synthesizing the hypnosis speech data with a virtual reality hypnosis scene, and outputting a virtual reality guide hypnosis speech.

In one embodiment, the processor 302 further performs the following operation when executing the computer program: performing a text language analysis, a grammatical analysis and a semantic analysis of the hypnosis guide language, so as to obtain information of words, word groups and sentences in the hypnosis guide language and information of relations between the words, the word groups and the sentences in the hypnosis guide language.

In one embodiment, the corpus data may be recorded by the user's susceptible person according to hypnosis speech features, and/or the corpus data may be recorded by the user's susceptible person at specified sampling rate and speech resolution.

In one embodiment, the corpus data may be recorded by the user's susceptible person with a dialect, and/or the corpus data may be recorded by the user's susceptible person with a personalized language.

In one embodiment, the processor 302 further performs the following operation when executing the computer program:

establishing and updating in real time the hypnosis speech library according to the corpus data recorded by the user's susceptible person, wherein a Hidden Markov Model is used to divide the corpus data in the hypnosis speech library, so as to construct the speech units;

using the Hidden Markov Model to select, splice and synthesize the found speech units.

The embodiments of the present disclosure further provide a computer readable storage medium, for improving the user's hypnosis susceptibility and optimizing the hypnosis effect, wherein the computer readable storage medium stores a computer program which causes the processor to perform the following operations when being executed:

performing a text analysis for a hypnosis guide language, so as to obtain text hierarchical information of the hypnosis guide language;

performing a speech analysis for the hypnosis guide language, so as to obtain speech rhythm information of the hypnosis guide language;

searching a hypnosis speech library for corresponding speech units, according to the text hierarchical information and the speech rhythm information of the hypnosis guide language, the hypnosis speech library storing speech units generated according to corpus data recorded by a user's susceptible person;

synthesizing found speech units into hypnosis speech data;

synthesizing the hypnosis speech data with a virtual reality hypnosis scene, and outputting a virtual reality guide hypnosis speech.

In one embodiment, the computer program further causes the processor to perform the following operation when being executed:

performing a text language analysis, a grammatical analysis and a semantic analysis of the hypnosis guide language, so as to obtain information of words, word groups and sentences in the hypnosis guide language and information of relations between the words, the word groups and the sentences in the hypnosis guide language.

In one embodiment, the corpus data may be recorded by the user's susceptible person according to hypnosis speech features, and/or the corpus data may be recorded by the user's susceptible person at specified sampling rate and speech resolution.

In one embodiment, the corpus data may be recorded by the user's susceptible person with a dialect, and/or the corpus data may be recorded by the user's susceptible person with a personalized language.

In one embodiment, the computer program further causes the processor to perform the following operation when being executed:

establishing and updating in real time the hypnosis speech library according to the corpus data recorded by the user's susceptible person, wherein a Hidden Markov Model is used to divide the corpus data in the hypnosis speech library, so as to construct the speech units;

using the Hidden Markov Model to select, splice and synthesize the found speech units.

In summary, based on the existed virtual reality hypnosis technology and in consideration that the language characteristics of different susceptibilities will have different influences on the user's hypnosis effect, the embodiments of the present disclosure combine the speech synthesis technology with the virtual reality hypnosis scene, improve the original standardized hypnosis speech (recorded by a professional announcer), and finally output the user's hypnosis susceptible guide speech, so as to achieve a more effective hypnosis state. The embodiments of the present disclosure provide a solution of automatic speech synthesis, and can output various hypnosis speeches having local features, thereby meeting the user requirement. On the other hand, by virtue of the speech synthesis technology, a standardized hypnosis-susceptible and specific hypnosis speech can be synthesized and output to finish the hypnosis process, thereby helping the user to better enter the hypnosis state.

The embodiments of the present disclosure can be applied to the virtual reality guide hypnosis process for the clinical breath control for the radiotherapies of thorax and abdomen tumor patients.

A person skilled in the art shall understand that the embodiment of the present disclosure can be provided as a method, a system or a computer program product. Therefore, the present disclosure can take the form of a full hardware embodiment, a full software embodiment, or an embodiment combining software and hardware aspects. Moreover, the present disclosure can take the form of a computer program product implemented on one or more computer usable storage mediums (including, but not limited to, a magnetic disc memory, CD-ROM, optical storage, etc.) containing therein computer usable program codes.

The present disclosure is described with reference to a flow diagram and/or block diagram of the method, device (system) and computer program product according to the embodiments of the present disclosure. It shall be understood that each flow and/or block in the flow diagram and/or block diagram and a combination of the flow and/or block in the flow diagram and/or block diagram can be realized by the computer program instructions. These computer program instructions can be provided to a general computer, a dedicated computer, an embedded processor or a processor of other programmable data processing device to generate a machine, such that the instructions performed by the computer or the processor of other programmable data processing devices generate the device for implementing the function designated in one flow or a plurality of flows in the flow diagram and/or a block or a plurality of blocks in the block diagram.

These computer program instructions can also be stored in a computer readable memory capable of directing the computer or other programmable data processing devices to operate in a specific manner, such that the instructions stored in the computer readable memory generate a manufactured article including an instruction device that implements the function(s) designated in one flow or a plurality of flows in the flow diagram and/or a block or a plurality of blocks in the block diagram.

These computer program instructions can also be loaded onto the computer or other programmable data processing devices, such that a series of operation steps is executed on the computer or other programmable devices to generate the processing realized by the computer, therefore the instructions executed on the computer or other programmable devices provide the steps for implementing the function designated in one flow or a plurality of flows in the flow chart and/or a block or a plurality of blocks in the block diagram.

The above specific embodiments further describe the objectives, technical solutions and beneficial effects of the present disclosure in details. It shall be appreciated that the above descriptions only illustrate the specific embodiments of the present disclosure, and are not used for limiting the protection scope of the present disclosure. Any modification, equivalent substitution and improvement made within the spirit and principle of the present disclosure shall be contained in the protection scope of the present disclosure.

What is claimed is:

1. A virtual reality guide hypnosis speech processing method, comprising:
performing a text analysis for a hypnosis guide language, so as to obtain text hierarchical information of relations between words, word groups and sentences in the hypnosis guide language;
performing a speech analysis for the hypnosis guide language, so as to obtain speech rhythm information in a phonetic level of the hypnosis guide language;
searching a hypnosis speech library for corresponding speech units, according to the text hierarchical information and the speech rhythm information of the hypnosis guide language, the hypnosis speech library storing speech units generated according to corpus data recorded by a user's susceptible person;
synthesizing found speech units into hypnosis speech data; and
synthesizing the hypnosis speech data with a virtual reality hypnosis scene, and outputting a virtual reality guide hypnosis speech;
wherein,
the text analysis for the hypnosis guide language comprises analyzing at least one of aspects of language level, grammatical level, and semantic level of the hypnosis guide language;
the speech analysis for the hypnosis guide language comprises analyzing at least one of timbre, intonation, and loudness of sounds corresponding to the hypnosis guide language; and
the hypnosis speech library is established and updated in real time according to the corpus data recorded by the user's susceptible person.

2. The method according to claim 1, wherein the corpus data is recorded by the user's susceptible person according to hypnosis speech features, and/or the corpus data is recorded by the user's susceptible person at a specified sampling rate and speech resolution.

3. The method according to claim 1, wherein the corpus data is recorded by the user's susceptible person with a dialect, and/or the corpus data is recorded by the user's susceptible person with a personalized language.

4. The method according to claim 1, wherein a Hidden Markov Model is used to divide the corpus data in the hypnosis speech library, so as to construct the speech units; and
wherein synthesizing found speech units into hypnosis speech data comprises using the Hidden Markov Model to select, splice and synthesize the found speech units.

5. A virtual reality guide hypnosis speech processing apparatus, comprising:
a memory,
a processor and
a computer program stored in the memory and executable in the processor,
wherein the processor performs the following operations when executing the computer program:
performing a text analysis for a hypnosis guide language, so as to obtain text hierarchical information of relation s between words, word groups and sentences in the hypnosis guide language;
performing a speech analysis for the hypnosis guide language, so as to obtain speech rhythm information in a phonetic level of the hypnosis guide language;
searching a hypnosis speech library for corresponding speech units, according to the text hierarchical information and the speech rhythm information of the hypnosis guide language, the hypnosis speech library storing speech units generated according to corpus data recorded by a user's susceptible person;
synthesizing found speech units into hypnosis speech data; and
synthesizing the hypnosis speech data with a virtual reality hypnosis scene, and outputting a virtual reality guide hypnosis speech;
wherein,
the text, analysis for the hypnosis guide language comprises analyzing at least one of aspects of language level, grammatical level, and semantic level of the hypnosis guide language;
the speech analysis for the hypnosis guide language comprises analyzing at least one of timbre, intonation, and loudness of sounds corresponding to the hypnosis guide language; and
the hypnosis speech library is established and updated in real time according to the corpus data recorded by the user's susceptible person.

6. The apparatus according to claim 5, wherein the corpus data is recorded by the user's susceptible person according to hypnosis speech features, and/or the corpus data is recorded by the user's susceptible person at a specified sampling rate and speech resolution.

7. The apparatus according to claim 5, wherein the corpus data is recorded by the user's susceptible person with a dialect, and/or the corpus data is recorded by the user's susceptible person with a personalized language.

8. The apparatus according to claim 5, wherein a Hidden Markov Model is used to divide the corpus data in the hypnosis speech library, so as to construct the speech units; and using the Hidden Markov Model to select, splice and synthesize the found speech units.

9. A non-transitory computer readable storage medium, wherein the non-transitory computer readable storage medium stores a computer program which causes a processor to perform the following operations when being executed:
performing a text analysis for a hypnosis guide language, so as to obtain text hierarchical information of relations between words, word groups and sentences in the hypnosis guide language;
performing a speech analysis for the hypnosis guide language, so as to obtain speech rhythm information in a phonetic level of the hypnosis guide language;
searching a hypnosis speech library for corresponding speech units, according to the text hierarchical information and the speech rhythm information of the hypnosis guide language, the hypnosis speech library storing speech units generated according to corpus data recorded by a user's susceptible person;
synthesizing found speech units into hypnosis speech data; and
synthesizing the hypnosis speech data with a virtual reality hypnosis scene, and outputting a virtual reality guide hypnosis speech;
wherein,
the text, analysis for the hypnosis guide language comprises analyzing at least one of aspects of language level, grammatical level, and semantic level of the hypnosis guide language;

the speech analysis for the hypnosis guide language comprises analyzing at least one of timbre, intonation, and loudness of sounds corresponding to the hypnosis guide language; and the hypnosis speech library is established and updated in real time according to the corpus data recorded by the user's susceptible person.

10. The non-transitory computer readable storage medium according to claim 9, wherein the corpus data is recorded by the user's susceptible person according to hypnosis speech features, and/or the corpus data is recorded by the user's susceptible person at a specified sampling rate and speech resolution.

11. The non-transitory computer readable storage medium according to claim 9, wherein the corpus data is recorded by the user's susceptible person with a dialect, and/or the corpus data is recorded by the user's susceptible person with a personalized language.

12. The non-transitory computer readable storage medium according to claim 9, wherein a Hidden Markov Model is used to divide the corpus data in the hypnosis speech library, so as to construct the speech units; and using the Hidden Markov Model to select, splice and synthesize the found speech units.

* * * * *